United States Patent [19]

Freidel et al.

[11] Patent Number: 4,993,573

[45] Date of Patent: Feb. 19, 1991

[54] BOTTLE CLOSURE

[75] Inventors: Iris Freidel, Creve Coeur, Mo.; Lev Leytes, Palo Alto, Calif.

[73] Assignee: Kinetek Systems, Inc., St. Louis, Mo.

[21] Appl. No.: 393,576

[22] Filed: Aug. 14, 1989

[51] Int. Cl.[5] ............................................ B65D 51/16
[52] U.S. Cl. .................................... 215/309; 215/276; 222/489
[58] Field of Search ................ 215/309, 276; 222/479, 222/489

[56] References Cited

U.S. PATENT DOCUMENTS

| | | | |
|---|---|---|---|
| 1,577,539 | 3/1926 | Polk | 215/309 |
| 2,191,495 | 2/1940 | Nesset | 215/309 |
| 3,499,568 | 3/1970 | Vinas Riera | 215/276 |
| 4,700,861 | 10/1987 | Neward | 215/309 |

*Primary Examiner*—Stephen Marcus
*Assistant Examiner*—Nova Stucker
*Attorney, Agent, or Firm*—Senniger, Powers, Leavitt & Roedel

[57] ABSTRACT

A bottle closure for sealingly closing a bottle while providing access to the interior of the bottle, the bottle being of the type having a neck with external threads thereon, and a mouth at the top of the neck. The bottle closure including a generally cylindric stopper having a radially outwardly projecting flange, a radially inwardly tapering lip projecting axially outwardly from one end of the stopper for insertion into the bottle through the mouth for sealing the bottle and at least one passageway extending through the stopper. The stopper has ears which are axially spaced from the flange. The flange and ears retain a cap on the stopper but allow the cap to rotate with respect to the stopper so that the cap may be tightened on and loosened from the threads of the bottle without unsealing the stopper from the bottle.

14 Claims, 2 Drawing Sheets

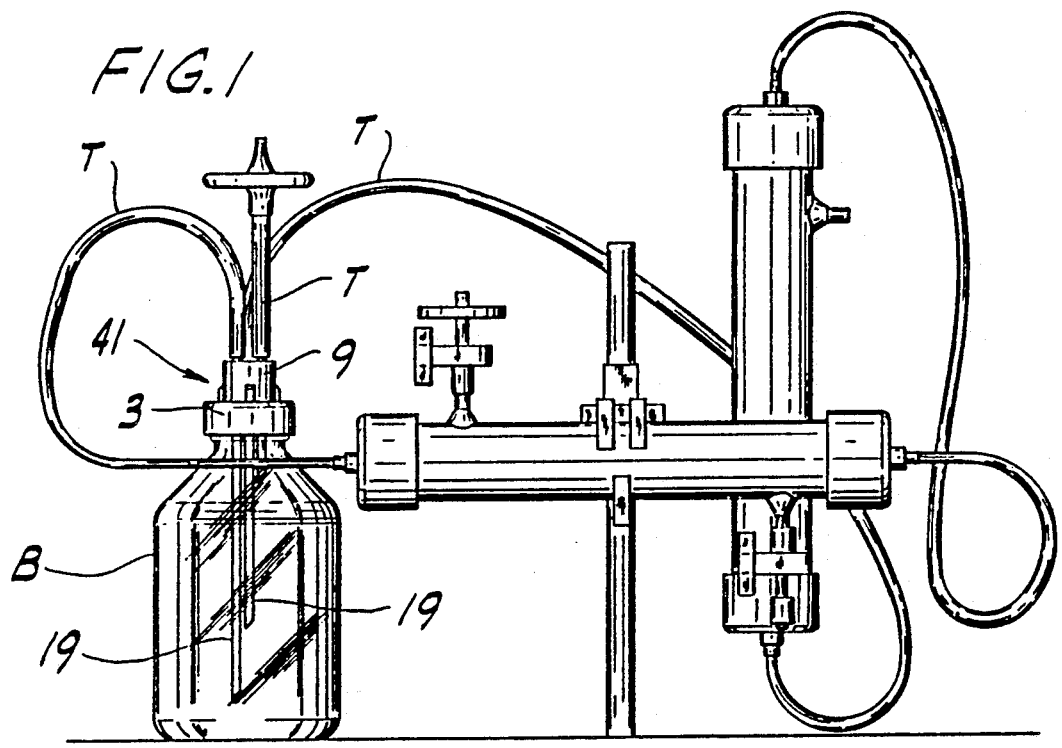
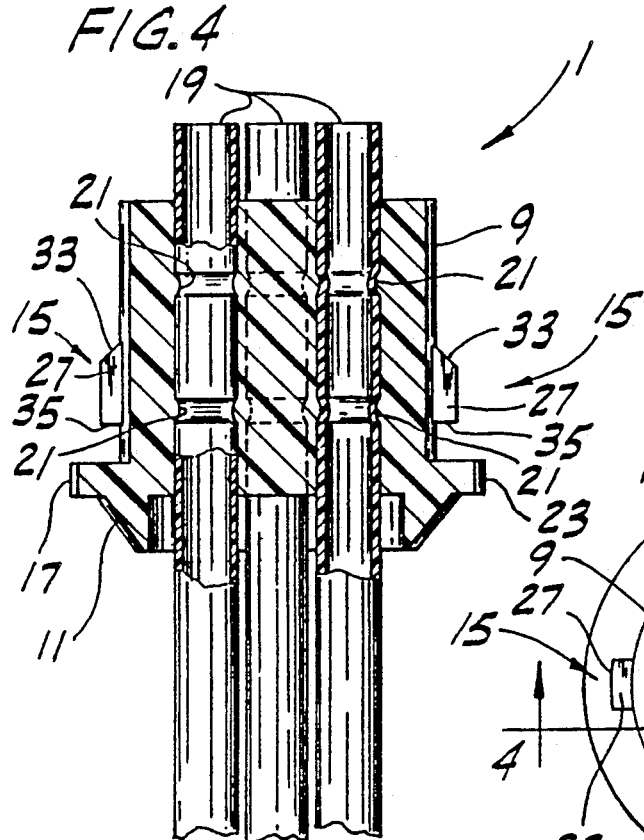
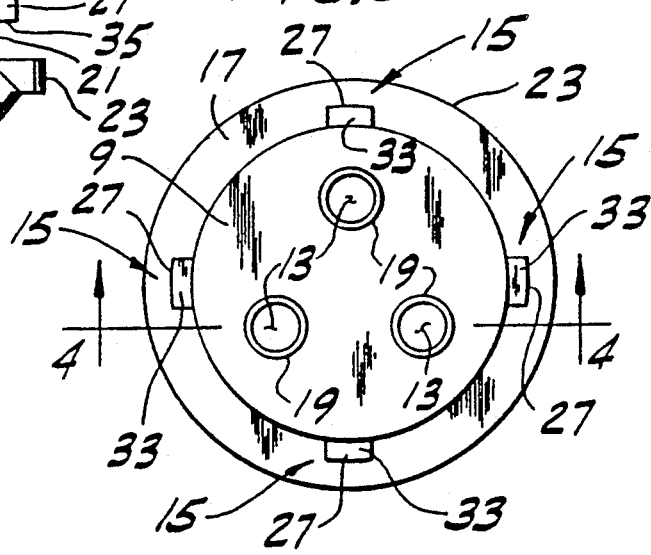

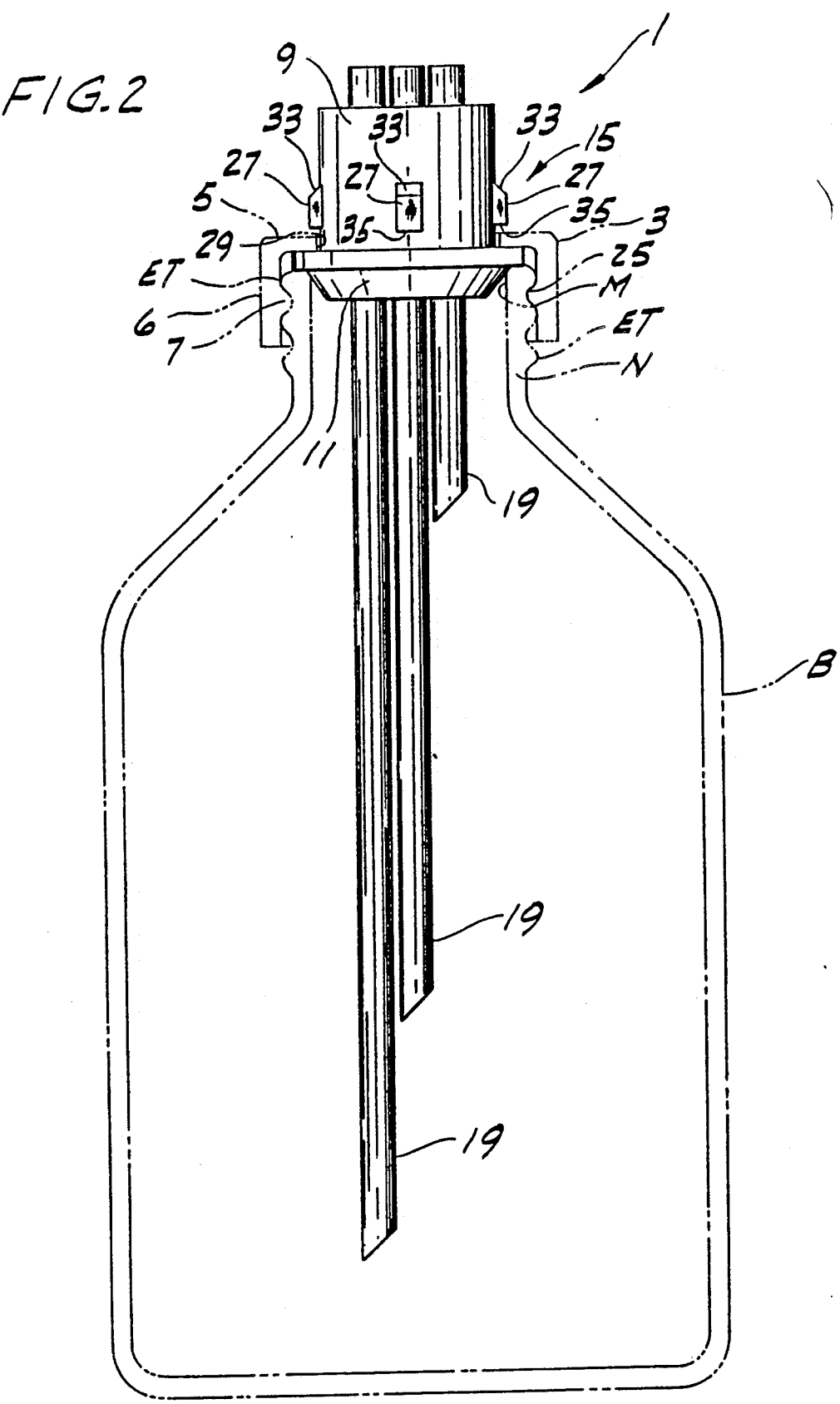

BOTTLE CLOSURE

BACKGROUND OF THE INVENTION

This invention relates to closures for a bottle, and more particularly to a bottle closure which provides controlled fluid communication with the interior of the bottle.

Bottles containing media of the kind used in certain medical and biomedical processes, such as cell culturing and the like, must be attached to laboratory equipment while remaining otherwise sealed from the atmosphere. To this end, bottle closures are provided which seal the bottle and yet provide for delivery of fluid to and/or from the interior of the bottle so that the bottle can be connected to a closed system of laboratory equipment for communication with the system while remaining sealed from the atmosphere. Communication with the interior of the bottle is provided by tubes extending through the closure or screwed into openings in the closure. The tubes may be sealed by cementing them in the closure with a sealant or molding them into the closure, however when bottles of different heights are used a tube cemented or molded in the closure cannot be adjusted vertically to compensate.

In order to securely attach the closure to the bottle and aid in sealing the bottle, a screw cap may be used in conjunction with the closure. The cap and closure are separate, with the cap applied to the closure before it is inserted into the bottle. When the cap is screwed onto the bottle, it engages the closure and holds it on the bottle, sealing the closure with the bottle. However, the cap also engages the closure when it is unscrewed from the bottle causing the closure to turn which tends to break the seal of the closure with the bottle. The turning of the closure also twists the tubes connecting the bottle to the laboratory equipment and disturbs the laboratory equipment.

SUMMARY OF THE INVENTION

Among the several objects of the present invention may be noted the provision of a bottle closure allowing access to the interior to the bottle by tubes or the like that can be adjusted to compensate for different sized bottles while remaining aseptically sealed with the closure; the provision of such a bottle closure which is autoclavable; and the provision of such a bottle closure which is economical to manufacture. It is also among the objects of this invention to Provide a bottle closure assembly which provides the aforementioned objects and which can be tightened on and loosed from the bottle without breaking the seal with the bottle or disturbing the laboratory equipment connected thereto.

Generally, a bottle closure constructed according to the principles of this invention sealingly closes a bottle while providing for delivery of fluid to and/or from the interior of the bottle, the bottle being of the type having a neck, and a mouth at the top of the neck. The bottle closure comprises a generally cylindric stopper having sealing means located generally at one end of the stopper for insertion into the mouth of the bottle for sealing the bottle and a plurality of passageways extending generally axially through the stopper. The passageways are adapted to slidingly but sealingly receive a tube therethrough for delivery of fluid to and/or from the interior of the bottle.

A bottle closure assembly constructed according to the principles of this invention includes a stopper as described and further a generally tubular cap having a radially inwardly projecting annular rim at one end. The cap is adapted for releasable connection to the bottle neck. The stopper has retainer means which retain the cap on the stopper. The cap is free to rotate with respect to the stopper so that the cap may be tightened on and loosened from the bottle neck without unsealing the stopper from the bottle.

Other objects and features will be in part apparent and in part pointed out hereinafter.

BRIEF DESCRIPTION OF THE DRAWINGS

FIG. 1 shows a cell culture kit including a bottle closure assembly of this invention;

FIG. 2 is a side view of a bottle closure with a bottle and screw cap shown in phantom;

FIG. 3 is a top view of a bottle closure; and

FIG. 4 is a section of the bottle closure taken in the plane including line 4—4 of FIG. 3.

Corresponding reference characters indicate corresponding parts throughout the several views of the drawings.

DETAILED DESCRIPTION OF A PREFERRED EMBODIMENT

Referring now to the drawings, a bottle closure of the present invention, indicated generally at 1, sealingly closes the bottle B while providing for delivery of fluid to and/or from the interior of the bottle of the type having a neck N with external threads ET, and a mouth M at the top of the neck. The bottle closure is adapted for use with a generally tubular cap 3 including an annular rim 5 at one end and a skirt 6 depending from the rim. The tubular cap 3 has internal threads 7 which may be engaged with the external threads ET of the cap for releasably connecting the cap to the bottle B.

The bottle closure 1 comprises a generally cylindric stopper 9 having a radially inwardly tapering lip 11 projecting generally axially outwardly from the periphery of one end of the stopper. The lip 11 is inserted into the mouth M of the bottle B; engages the interior surface of the bottle and sealing the stopper 9 with the bottle. In addition to its sealing function, the tapered lip 11 also aids in positioning the stopper in the mouth M of the bottle. The lip 11 constitutes sealing means in this embodiment. The bottle closure 1 further comprises at least one Passageway 13 extending generally axially through the stopper 9. It is within the scope of this invention to provide a plurality of such passageways, with the preferred embodiment, as shown in the drawings, having three passageways 13. An upper retainer member, generally indicated at 15, and lower retainer member 17 on the stopper 9 are adapted to retain the rim 5 of the cap between them to retain the cap on the stopper 9. The upper and lower retainer members constitute retainer means in this embodiment. The upper and lower retainer members allow the cap to rotate with respect to the stopper, and they also allow the cap to move axially of the stopper between them so that the cap may be tightened on and loosened from the threads ET without moving the stopper and unsealing the stopper from the bottle B.

The stopper 9, which is preferably made of resilient material, is adapted to slidingly but sealingly receive a tube 19 through each passageway 13. The outside diameter of the tube 19 is nominally the same as the diameter of the passageway 13 in which it is inserted so that there is a relatively close fit of the tube in the passageway and yet the tube may be relatively easily inserted into the passageway. Two ring-like strictures 21 in each passageway 13 are axially spaced relative to each other and have in this embodiment a nominal diameter approximately 0.030 inches smaller than the outside diameter of the tube 19. The strictures 21 engage the tube 19 inserted into the passageway 13 for a tight, aseptic seal of the stopper 9 with the tube but still allow the tube to slide in the passageway so that the length of tube extending into the bottle B may be varied according to the height of the bottle being closed while keeping the tube sealed in the passageway. The strictures 21 in each passageway 13 constitute tube sealing means in this embodiment.

The lower retainer member 17 comprises a radially outwardly projecting flange 23 located generally adjacent the end of the stopper including the lip 11. The flange 23 extends sufficiently radially outwardly so that when the stopper 9 is inserted into the bottle, the flange 23 engages a top portion of the bottle neck N surrounding the mouth M, but the diameter of the flange is less than the inner diameter of the caP 3 so that the cap fits over the flange when screwed onto the bottle B. However, the annular rim 5 of the cap engages the upper surface of the flange 23 when the cap moves axially downward and prevents the cap 3 from sliding down off of the stopper 9. Further, the engagement of the rim 5 with the flange 23 forces the flange down against the top portion of the bottle neck N when the cap is screwed onto the bottle B which securely holds the stopper 9 on the bottle. The forced engagement of the flange 23 with the bottle neck N compresses the flange against the bottle neck and seals the bottle. The sealing function of the flange 23 is in addition to the sealing function of the lip 11 of the stopper so that when the cap 3 is loosened from the bottle B, the stopper 9 remains sealed with the bottle. The threads ET, 7 on the bottle B and the cap 3 are shown as screw threads in this embodiment, but it is within the scope of this invention to connect the cap to the bottle by other fastening designs such as a bayonet type fastener.

The stopper has a plurality of radially outwardly projecting ears 27, constituting the upper retainer member 15, which are circumferentially spaced around the stopper 9 in a plane perpendicular to the axis of the stopper. The cap 3 is disposed on the stopper with the marginal edge 29 of its annular rim 5 retained between the ears 27 and the flange 23 of the stopper. The internal diameter of the annular rim 5 is greater than the diameter of the stopper 9 so that the cap is free to rotate with respect to the stopper and the axial separation of the ears and flange allows the cap to move axially between them. Therefore, the cap 3 may be tightened on and loosened from the bottle B without turning the stopper 9 does not disturb the seal of the lip 11 of the stopper with the bottle or cause unwanted movement of laboratory equipment connected to the bottle via the tubes 19. This is of particular advantage when the bottle B, which is attached to other laboratory equipment, has been emptied of its contents and the stopper 9 is to be transferred to another bottle. The cap 3 may be tightened on and loosened from the bottle B without disturbing the stopper 9 and the stopper may then be carefully be pulled out of the bottle, inserted into the other bottle and secured to that bottle.

The stopper 9 is designed so that the cap 3 can be fitted on the stopper to be retained on the stopper for ease in securing the closure 1 to a bottle. The ears 27 of the stopper 9 each have an upper surface 33 and a lower surface 35, with the upper surface being beveled and the lower surface lying generally in a plane perpendicular to the axis of the stopper. The cap 3 may be applied to the stopper 9 to be retained thereon by forcing the cap down over the top of the stopper so that the marginal edge 29 of the rim 5 of the cap engages the upper surface 33 of the ears 27. The engagement of the cap rim 5 with the beveled upper surface 33 causes the ears 27 to be resiliently compressed radially inwardly as the cap 3 is forced downwardly for snapping the cap over the ears. Thereafter, the rim 5 may engage the ears 27 only on their lower surfaces 35, which is a generally flush engagement that retains the cap 3 on the stopper 9.

A bottle closure assembly of this invention, generally indicated at 41, includes the combination of the stopper 9 and the cap 3, or alternatively the stopper 9, cap 3 and tubing 19.

FIG. 1 shows a bottle closure assembly, generally indicated at 41, as used in a cell culture kit to sealingly close a bottle B containing media carrying nutrients for the cells. The cell culture kit shown in FIG. 1 is one which utilizes hollow fiber membranes which permit the ingress of culture medium, oxygen and other nutrients for cell growth as well as removal of the desired product and waste products of cell growth. Such cell culture devices are know to the art and are described in the patent literature (see, for example, U.S. Pat. Nos. 4,200,689 and 4,206,015).

The lip 11 of the stopper 9 is flexible and is sized to seal in 100 ml or larger wide neck medium bottles. The stopper 9, once inserted into the bottle, provides a pressure and vacuum tight seal which also maintains an aseptic environment in the bottle. The stopper 9 has three passageways 13 with a relatively rigid, Polypropylene tube 19 inserted in each passageway for connection to a feed line, a return line and a vent line respectively. The tubes 19 may be adjusted as necessary depending upon the height of the bottle being used. Flexible tubing T, which may be used to connect the tubes 19 to the stated feed, return and vent lines, can be attached directly to the rigid tubing 19 without additional fittings, thus minimizing the number of connections and the chance for leaks.

When the media stored in the bottle is exhausted, the cap 3 of the closure assembly is unscrewed from the bottle, the stopper pulled out of the bottle and the closure assembly 41 is then attached to a new bottle. During transfer, the skirt 6 of the cap 3 covers portions of the stopper, including the lips 11, which are exposed to the growth media inside the bottle when the stopper is inserted into the mouth of the bottle. Therefore, those portions are protected from inadvertent contact with the skin of a person transferring the stopper which could contaminate the stopper and destroy the aseptic environment in the bottle. The stopper, in this embodiment, is made of medical grade, silicone rubber having a durometer hardness of approximately 65 shor. It will be understood that the stopper of this invention may be made of material having a hardness falling within a range of values. The stopper is steam autoclavable for repeated use in sterile applications such as cell cultures. However, the stopper is equally adapted for non-sterile applications such as high pressure liquid chromatography (HPLC).

As various changes could be made in the above constructions without departing from the scope of the invention, it is intended that all matter contained in the above description or shown in the accompanying drawings shall be interpreted as illustrative and not in a limiting sense.

What is claimed is:

1. A bottle closure for sealingly closing a bottle while providing for delivery of fluid to and/or from the interior of the bottle, the bottle being of the type having a neck and a mouth at the top of the neck, the bottle closure comprising a generally cylindric stopper having sealing means generally at one end of the stopper for insertion into the bottle through the mouth for sealing the bottle and a plurality of passageways extending generally axially through the stopper, each passageway having tube sealing means therein for slidingly but sealingly engaging a tube received therethrough for delivery of fluid via the tube to and/or from the interior of the bottle, said tube sealing means being adapted to form an aseptic seal with the tube engaged thereby, said tube sealing means comprising a plurality of ring-like strictures in each passageway, the strictures being axially spaced relative to each other in each passageway.

2. The bottle closure as set forth in claim 1 wherein the stopper is autoclavable.

3. A bottle closure for sealingly closing a bottle while providing for delivery of fluid to and/or from the interior of the bottle, the bottle being of the type having a neck and a mouth at the top of the neck, the bottle closure being adapted for use with a generally tubular cap adapted for releasable connection to the bottle and having an inwardly projecting annular rim at one end thereof, the bottle closure comprising a generally cylindric stopper having sealing means generally at one end thereof, said sealing means being adapted for insertion into the mouth of the bottle with said sealing means engaging the interior of the bottle and sealing the bottle, at least one passageway extending generally axially through the stopper, and retainer means adapted for retaining the cap on the stopper and for allowing the cap to rotate with respect to the stopper so that the cap may be tightened on and loosened from the bottle without unsealing the stopper from the bottle, said retainer means comprising upper and lower retainer members, the lower retainer member comprising a radially outwardly projecting flange located generally adjacent the end of the stopper with said sealing means, the flange being engageable with a portion of the neck surrounding the mouth, the flange being adapted to be engaged by the rim of the cap when said cap is connected to the bottle so that the flange is held in sealing engagement with the bottle neck.

4. The bottle closure as set forth in claim 3 wherein the stopper has a plurality of passageways therethrough and is adapted to slidingly and sealingly receive a tube through each passageway.

5. The bottle closure as set forth in claim 4 wherein the stopper has tube sealing means in each passageway for sealingly but slidingly engaging a tube received therethrough.

6. The bottle closure as set forth in claim 5 wherein each tube sealing means is adapted to form an aseptic seal with the tube engaged thereby.

7. The bottle closure as set forth in claim 6 wherein said tube sealing means comprises a plurality of ring-like strictures in each passageway, the strictures being axially spaced relative to each other in each passageway.

8. The bottle closure as set forth in claim 3 wherein the stopper is autoclavable.

9. The bottle closure as set forth in claim 3 wherein said sealing means comprises an annular lip projecting axially outwardly from the end of the stopper, the lip tapering radially inwardly toward its axially outer end for facilitating insertion of the stopper into the mouth of the bottle.

10. A bottle closure assembly for sealingly closing a bottle while providing for delivery of fluid to and/or from the interior of the bottle, the bottle being of the type having a neck, and a mouth at the top of the neck, the bottle closure assembly comprising a generally cylindric stopper having retainer means, sealing means generally at one end of the stopper for insertion into the mouth of the bottle for sealing the bottle and at least one passage extending generally axially through the stopper, the passage having tube sealing means therein adapted to slidingly engage a tube received in the passageway while forming an aseptic seal with the tube, said tube sealing means comprising a plurality of ring-like strictures in the passageway, the strictures being axially spaced relative to each other in the passageway, and a generally tubular cap having a radially inwardly projecting rim at one end thereof, the cap being adapted to be releasably connected to the bottle neck, said retainer means retaining the cap on the stopper, the cap being free to rotate with respect to the stopper so that the cap may be tightened on and loosened from the bottle without unsealing the stopper from the bottle.

11. The bottle closure assembly as set forth in claim 10 further comprising a plurality of tubes each being receivable through a respective passageway in the stopper and wherein the diameter of each passageway is nominally the same as the outside diameter of the tube received therethrough.

12. A bottle closure assembly for sealingly closing a bottle while providing for delivery of fluid to and/or from the interior of the bottle, the bottle being of the type having a neck, and a mouth at the top of the neck, the bottle closure assembly comprising a generally cylindric stopper having retainer means including upper and lower retainer members, said upper retainer member comprising a plurality of radially outwardly projecting ears, sealing means generally at one end of the stopper for insertion into the mouth of the bottle for sealing the bottle and at least one passage extending generally axially through the stopper, and a generally tubular cap having a radially inwardly projecting rim at one end thereof, the cap being adapted to be releasably connected to the bottle neck, said retainer means retaining the cap on the stopper, the cap being free to rotate with respect to the stopper so that the cap may be tightened on and loosened from the bottle without unsealing the stopper from the bottle.

13. The bottle closure assembly as set forth in claim 12 wherein each ear has an upper surface and a lower surface, said upper surface being beveled and said lower surface lying generally in a plane perpendicular to the axis of the stopper so that the cap is applied to the stopper by forcing the cap down over the ears, the beveled upper surface of the ear engaging the rim of the cap and resiliently compressing the ears radially inwardly as the cap is forced downwardly for snapping the cap over the ears, the lower surface of the ears being engageable with the marginal edges of the rim flush when the cap is moved upward for retaining the cap on the stopper.

14. The bottle closure as set forth in claim 12 wherein said lower retainer member comprises a radially outwardly projecting flange located generally adjacent the end of the stopper including said sealing means, the flange having sufficient radial extension so that the flange engages a top portion of the neck surrounding the mouth, the flange being adapted to be engaged by the rim of the cap when said cap is connected to the bottle thereby holding the flange in sealing engagement with the bottle neck.

* * * * *